(12) United States Patent
Pflum et al.

(10) Patent No.: US 10,314,735 B2
(45) Date of Patent: Jun. 11, 2019

(54) PROTECTIVE SPLINT KIT FOR THE TREATMENT OF JOINT PAIN AND WOUNDS

(71) Applicants: Patricia A. Pflum, Redbank, NJ (US); Francis A. Pflum, Redbank, NJ (US)

(72) Inventors: Patricia A. Pflum, Redbank, NJ (US); Francis A. Pflum, Redbank, NJ (US)

(*) Notice: Subject to any disclaimer, the term of this patent is extended or adjusted under 35 U.S.C. 154(b) by 0 days.

(21) Appl. No.: 15/206,810

(22) Filed: Jul. 11, 2016

(65) Prior Publication Data

US 2016/0317344 A1 Nov. 3, 2016

Related U.S. Application Data

(60) Provisional application No. 62/195,838, filed on Jul. 23, 2015.

(51) Int. Cl.
| | |
|---|---|
| *A61F 5/058* | (2006.01) |
| *A61F 17/00* | (2006.01) |
| *A61F 15/00* | (2006.01) |
| *A61F 13/00* | (2006.01) |
| *A61F 5/10* | (2006.01) |
| *A61F 13/10* | (2006.01) |

(52) U.S. Cl.
CPC ...... *A61F 5/05875* (2013.01); *A61F 5/05825* (2013.01); *A61F 5/05841* (2013.01); *A61F 13/00076* (2013.01); *A61F 15/001* (2013.01); *A61F 17/00* (2013.01); *A61F 5/10* (2013.01); *A61F 13/104* (2013.01); *A61F 2013/00089* (2013.01)

(58) Field of Classification Search
CPC .... A61F 5/0118; A61F 5/058; A61F 5/05825; A61F 5/05866; A61F 5/05875; A61F 5/10; A61F 13/10; A61F 13/104; A61F 13/105; A61F 17/00
USPC ................................................. 602/6, 22, 30
See application file for complete search history.

(56) References Cited

U.S. PATENT DOCUMENTS

| | | | |
|---|---|---|---|
| 1,612,267 A | 12/1926 | Dickson | |
| 3,357,425 A * | 12/1967 | Burton | A61F 13/0273 206/440 |
| 4,628,917 A * | 12/1986 | Campagna, Jr. | A61F 13/04 602/8 |
| 5,925,008 A * | 7/1999 | Douglas | A61F 5/05875 128/880 |
| 7,985,192 B2 * | 7/2011 | Sheehan | A61F 5/01 602/5 |
| 8,211,044 B2 | 7/2012 | Liebowitz | |
| 8,951,217 B2 * | 2/2015 | Joseph | A61F 5/01 602/20 |
| 2006/0206047 A1 | 9/2006 | Lampe et al. | |
| 2009/0105625 A1 | 4/2009 | Kohner et al. | |
| 2015/0282976 A1 * | 10/2015 | Liddle | A61F 5/05841 602/7 |

* cited by examiner

*Primary Examiner* — Keri J Nelson
(74) *Attorney, Agent, or Firm* — Keith D. Nowak; Carter Ledyard & Milburn LLP

(57) ABSTRACT

A kit for assembling a device designed to prevent flexing of a joint to reduce joint pain or to prevent reopening of a wound over said joint. The kit allows a user to assemble a device of any desired size or shape.

3 Claims, 6 Drawing Sheets

PROTECTIVE SPLINT KIT FOR THE TREATMENT OF JOINT PAIN AND WOUNDS

FIELD OF THE INVENTION

The present invention generally relates to a medical device for treating joint pain or wounds on joints and, more specifically, to a kit which allows the user to create a dressing that will alleviate joint pain by restricting flexing of the joint and/or prevent a wound situated over a joint from re-opening due to flexing of the joint.

BACKGROUND OF THE INVENTION

Wound dressings of various kinds and different levels of effectiveness have existed throughout history. However, it wasn't until 1920, after the First World War was over, before there was an effective bandage for simple injuries that didn't need to be stitched. The wound dressing we all know as the Band-Aid was invented in 1920 by Earle Dickson, a Johnson & Johnson employee. On Dec. 28, 1926, Mr. Dickson was awarded U.S. Pat. No. 1,612,267 for his invention.

Since 1920, the Band-Aid, and wound dressings in general, have seen little improvement, despite the issuance of a number of patents, and the filing of patent applications in the field. For example, U.S. application 2009/0105625, is directed to a toe and finger guard that includes a protective member bendable from an initial, generally plainer, shape, to a curved shape, when mounted on a digit to be protected. U.S. application 2006/0206047 describes a bandage consisting of a shaped laminated sheet with an interior layer of absorbent material for absorbing moisture and wound exudate, an exterior layer of loop material on the exterior side of the bandage, and a splint of a stiffer material sandwiched between two of the layers. U.S. Pat. No. 8,211,044 is directed to a bandage comprising a sheath that fits around at least a portion of the circumference of a finger, optionally comprising a pouch for retaining an insert.

All of the references cited above generally cover a bandage of standard sizes and shapes which are provided to the consumer as a complete product. Therefore, if the bandage is not provided in the right shape or size to address a specific wound, the bandage can be useless to the consumer. This is particularly true for wounds over joints in the body such as finger joints, elbows, knees etc. When there is a wound over a joint it is often necessary to prevent the joint from flexing so the wound will heal. Also, there is often joint pain without a wound, and it is necessary to prevent the joint from flexing to avoid joint pain. In order to have a bandage that can be adapted to various joints in the body, standard sized bandages will not always be effective. Therefore, it is necessary to provide the consumer with the means to create a custom bandage to prevent a joint from flexing to prevent joint pain, and/or to prevent a joint from flexing so a wound over a joint will not re-open.

SUMMARY OF THE INVENTION

A kit that allows a user to assemble a completed device that when applied will prevent flexing of a joint to minimize joint pain or to prevent re-opening of a wound situated over a joint. The kit consists of three components, a fabric material with adhesive on one side, a semi-rigid material either pre-bent to a desired shape, or bendable to function as a splint, and a non-adhesive fabric. The kit allows a user to assemble the three components to create a device of any desirable size or shape.

DETAILED DESCRIPTION

The invention described herein is directed to a kit that allows a user of the kit to assemble a completed device that when applied, will alleviate pain by restricting the movement of a painful joint and/or restrict movement of a joint to prevent a reopening of a wound situated over a joint.

The inventive kit has three components. The first component is a fabric material with adhesive on only one side. The second component is a semi-rigid material that is either pre-bent to a desired shape or bendable. The second component functions as a splint and once bent the second component retains its shape throughout the normal stresses of daily use when the device assembled from the inventive kit is applied to a joint. The third component is a non-adhesive fabric.

Figure 4:
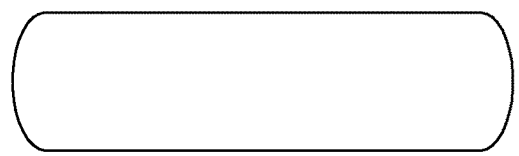
FIG. 4 shows a band-aid sized version of the first component with fabric adhesive on only one side with the adhesive side on the top surface.
Figure 5:
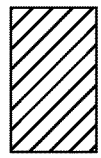
FIG. 5 shows one size of the second component, a semi-rigid material flat, pre-bent or bendable.
Figure 6:
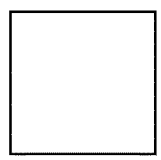
FIG. 6 shows one size of the third component, a fabric, being non-adhesive on one side.
Figure 7:
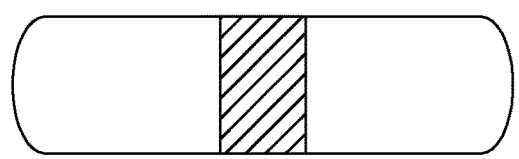
FIG. 7 shows the second component being placed on component 1.
Figure 8:
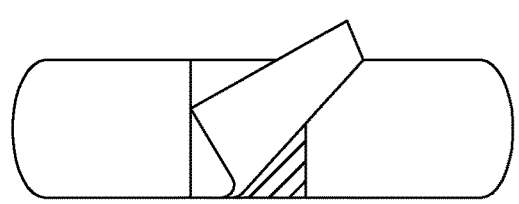
FIG. 8 shows the third component being placed upwards on top of the second component, covering the same; and adhering to the adhesive side of the first component.

To assemble a device for application to a painful joint or a wound situated over a joint, the user first places the second component on the first component and then covers the first two components with the third component. The three components are illustrated in FIGS. 4-6, respectively. FIG. 7 illustrates the placement of the second component on the first component. FIG. 8 illustrates the placement of the third component over the first and second components. As the first component is adhesive on its upper portion, the second component is adhered to the first component upon placement of the second component, the third component is also adhered to the first component upon placement of the third component. It is important to note that the third component is designed to be large enough to completely cover the second component.

Figure 1:
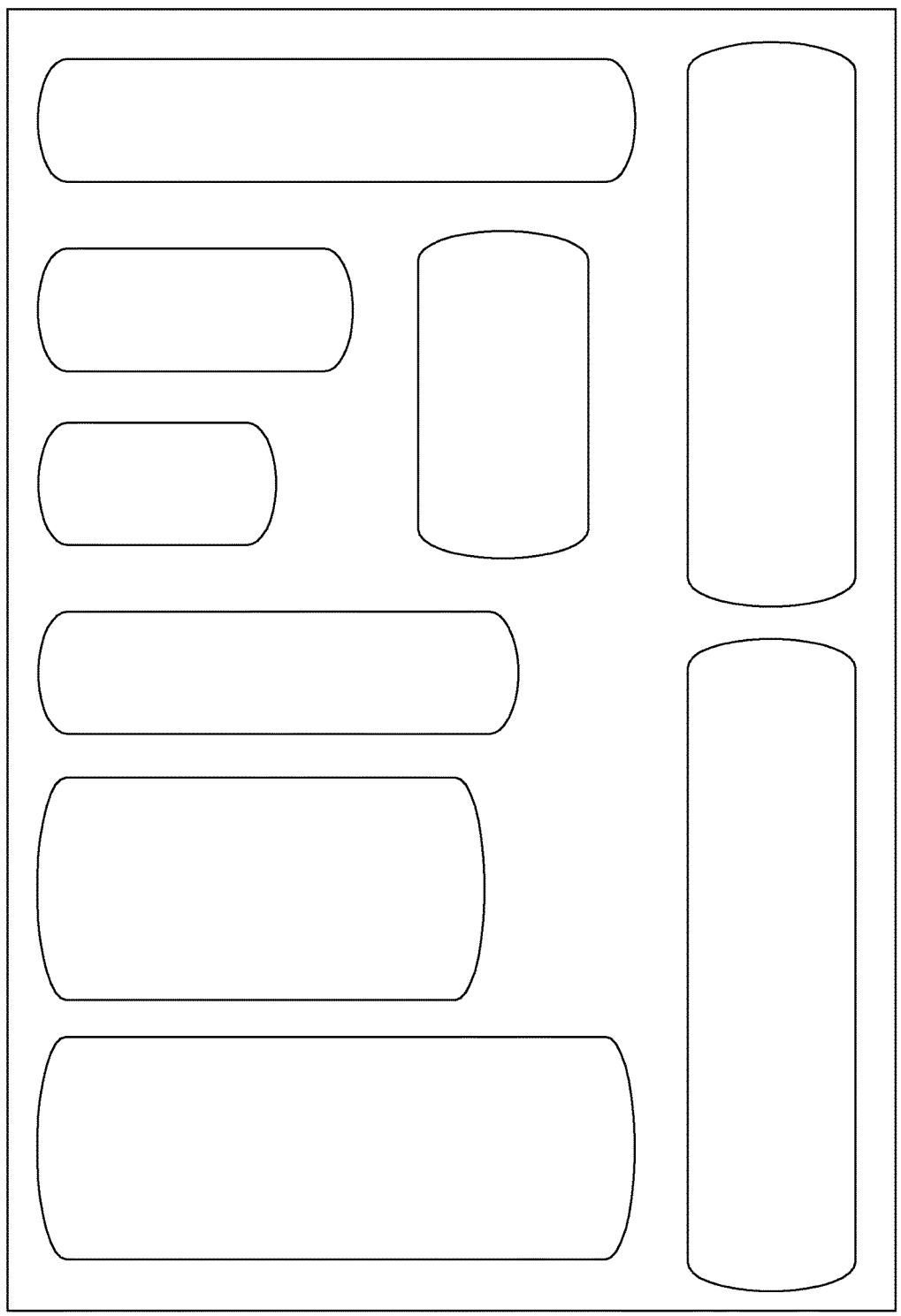
FIG. 1 shows a first component of the inventive kit consisting of adhesive cloth material from which various sizes of the first component can be selected.
Figure 2:
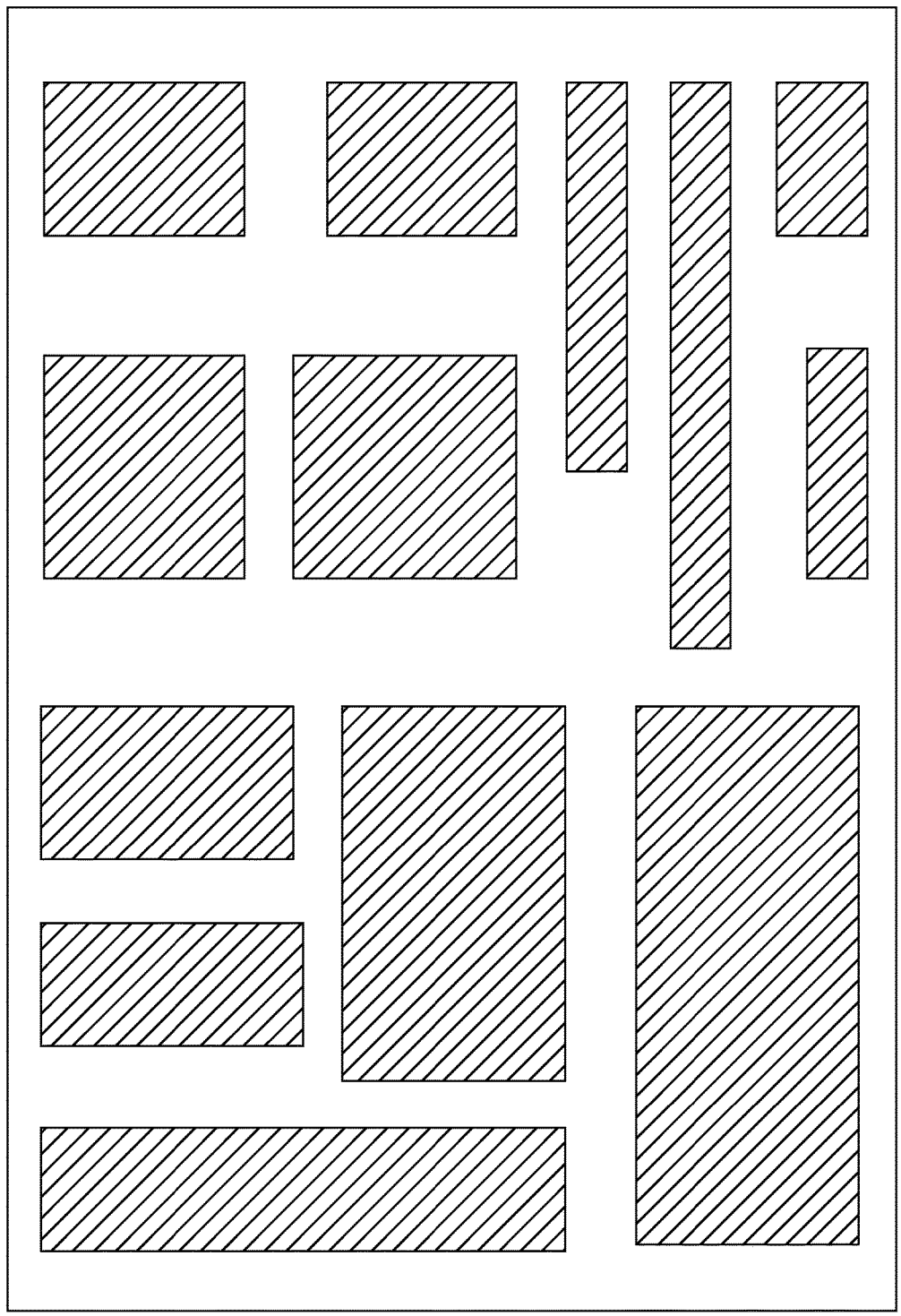
FIG. 2 shows a second component of the inventive kit consisting of semi-rigid material from which various sizes of the second component can be selected.
Figure 3:
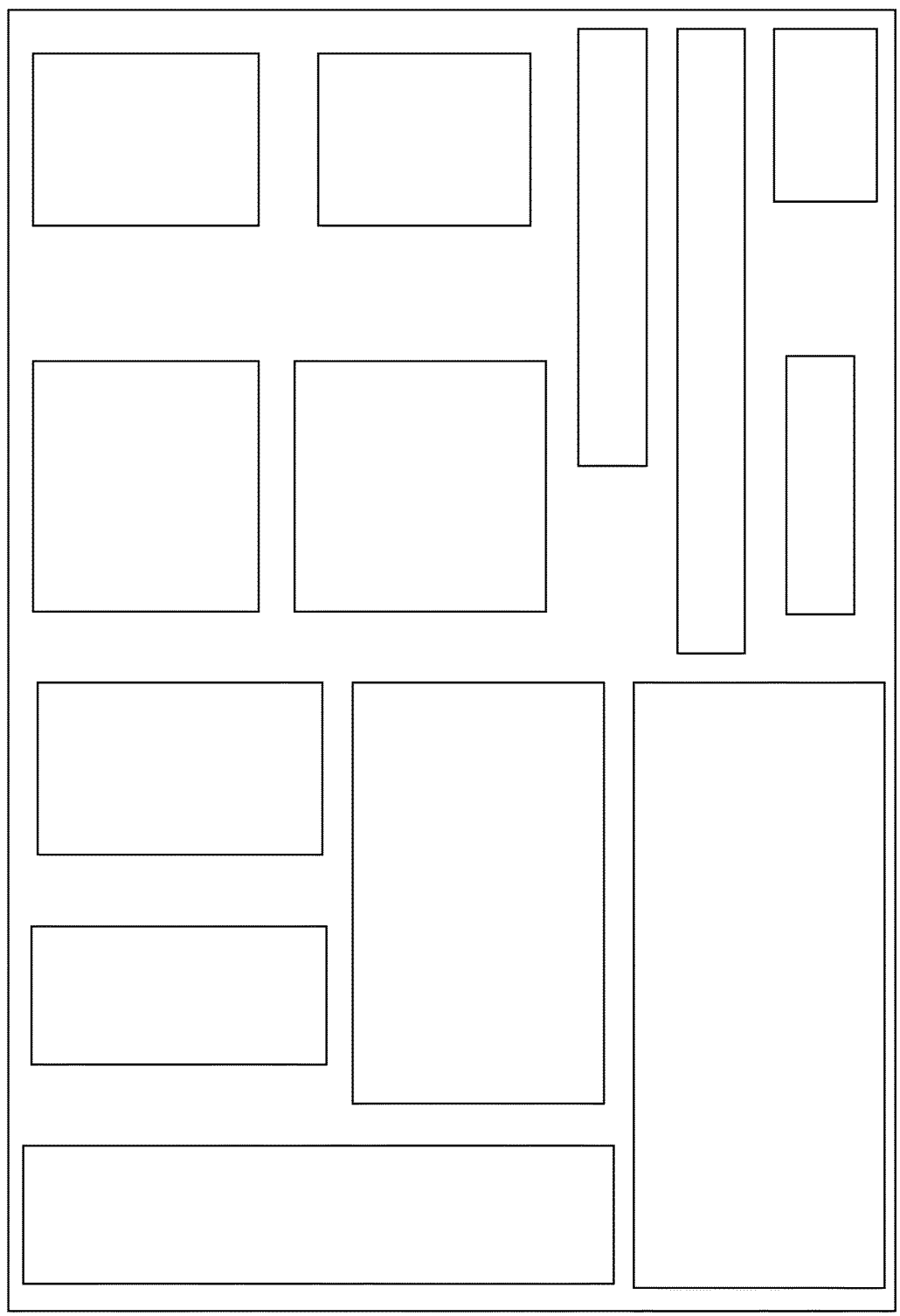
FIG. 3 shows a third component of the inventive kit consisting of non-adhesive material from which various sizes of the third component can be selected.

The kit of the present invention is designed to be used in connection with joints/wounds of various sizes and in various locations on the body of the subject being treated, which includes the human body and also the body of other species. In order to accommodate the need for a device of various sizes and placement on various locations on the subject's body, the kit of the present invention allows the user to select from a variety of sizes and shapes for all three components as illustrated in FIGS. 1-3. FIG. 1 shows that the kit includes various sizes and shapes for the first component. FIG. 2 shows that the kit includes sizes and shapes for the second component, and FIG. 3 shows that the kit includes various sizes and shapes for the third component. It should also be understood that a user could select from the shapes and sizes of all three components shown in FIGS. 1-3, or cut a shape and size to suit a particular joint or wound location.

Figure 9:
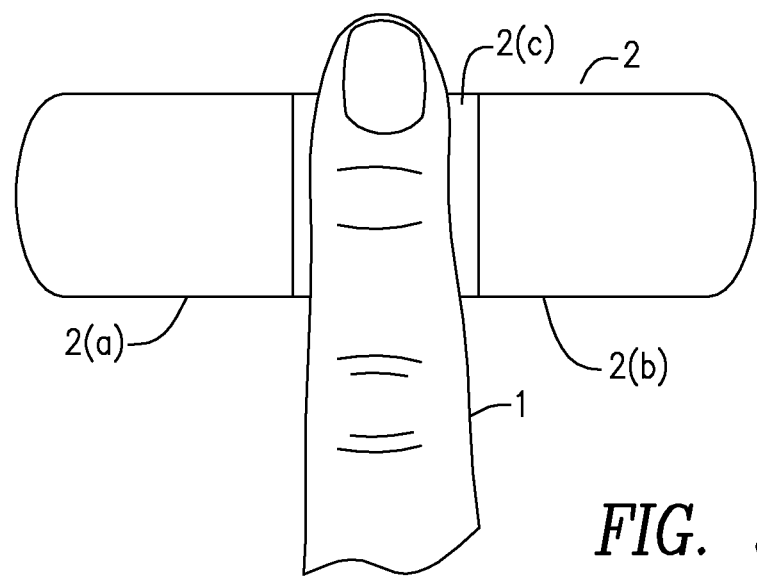
FIG. 9 shows an extremity (finger) being placed in such a way that the second component covers the joint. The skin of the extremity does not contact the second component.
Figure 10:
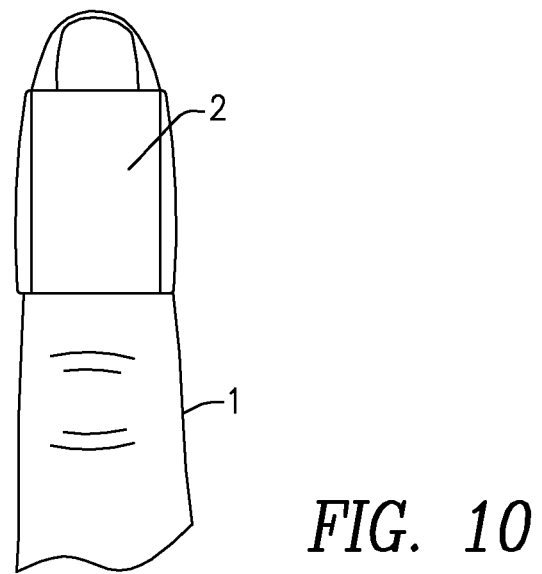
FIG. 10 shows the invention applied to the extremity with the adhesive side of the first component on the skin, once applied the motion of the joint is restricted.

Referring now to FIG. 9 there is shown a completed device 2 being applied to a finger 2 and designed to cover the first joint on the finger. The upper surface (2(a) and 2(b)) of the device 2 in FIG. 9 is the adhesive portion of the first component and 2(c) is the upper surface of the third component. The second component is underneath 2(c). FIG. 10 shows the device being secured around finger 1 by use of adhesive portions 2(a) and 2(b).

Figure 11:
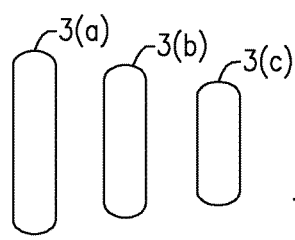
FIG. 11 illustrates an example of different sized second components in the inventive kit.
Figure 12:
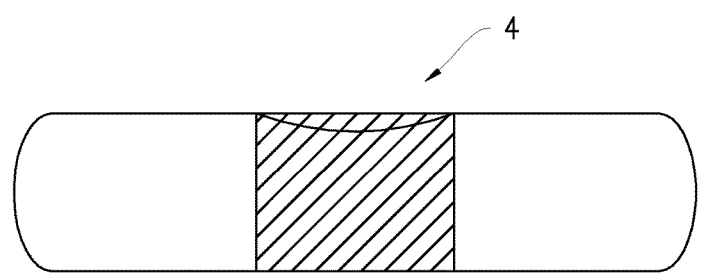
FIG. 12 shows the adhesive first component and the adherent third component pre-sized and pre-attached into which one or more of the second components may be inserted.
Figure 13:
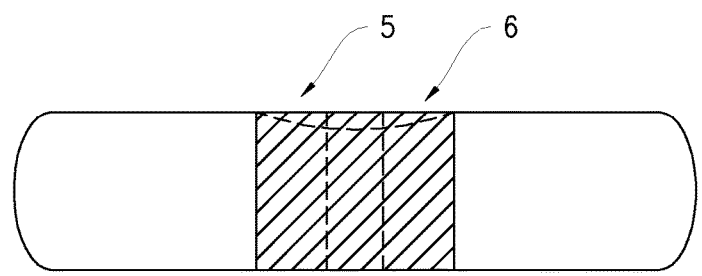
FIG. 13 shows an example of the second component in a pre-fabricated, adhesive and non-adherent, pre-attached pocket.
Figure 14:
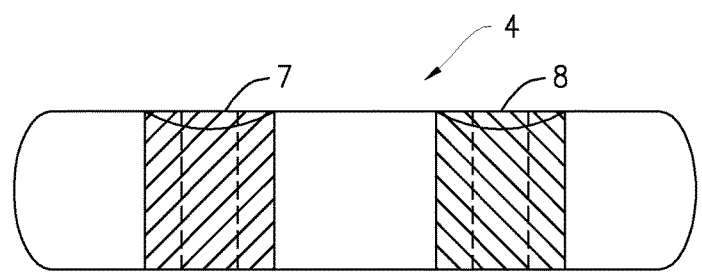
FIG. 14 shows the adhesive first component with two non-adherent, pre-attached third components with pockets into which the second component has been inserted.

FIG. 11 illustrates three possible sizes, 3(a), 3(b) and 3(c) of the second component which is the splint for use with the device assembled from the inventive kit. FIG. 12 illustrates the use of a pouch 4 into which a second component splint can be inserted. Similarly, FIGS. 13 and 14 illustrate the use of two pouches 5 and 6 and/or pouches 7 and 8 in different locations on the device assembled from the inventive kit.

The kit of the present invention allows a user to create a device of any size or shape to be applied to any joint, in any location, and/or any wound covering a joint, for the subject being treated. The use of the second component splint will prevent flexing of the joint to alleviate joint pain and/or prevent flexing of the joint to prevent reopening of a wound situated over a joint. The foregoing description is merely illustrative and not limiting, having been presented by way of example only. Although examples have been shown and described, it will be apparent to those with ordinary skill in the art that changes, modifications, and/or modifications, and/or alterations, can be made. Throughout this description, the embodiments and examples shown should be considered as exemplars, rather than limitations on the apparatus and methods disclosed or claimed.

The invention claimed is:

1. A method for utilizing a three component kit to assemble a device that prevents flexing of a joint to minimize joint pain and prevents re-opening of a wound situated over said joint, comprising,
providing a first sheet of a first fabric component having a first outline of first various predetermined shapes and sizes, a second sheet of a second semi-rigid material having a second outline of second various predetermined shapes and sizes, and a third sheet of a third non-adhesive fabric component having a third outline of third various predetermined shapes and sizes,
cutting a first kit element from said first sheet of said first fabric component by either cutting along said first outline or cutting a first shape and size required for a particular application, where the first shape or size is not included in the first various predetermined shapes and sizes, said first fabric component having adhesive only on a top surface of said first fabric component,
cutting a second kit element from said second sheet of said second semi-rigid material by either cutting along said second outline or cutting a second shape or size required for a particular application, where the second shape or size is not included in the second various predetermined shapes and sizes,
said second kit element being smaller than said first kit element and being adhered to a first portion of said adhesive top surface of said first kit element,
cutting a third kit element from said third sheet of said third non-adhesive fabric component by either cutting along said third outline or cutting a third shape and size required for a particular application, where the third shape or size is not included in the third various predetermined shapes and sizes,
said third kit element being adhered to a second portion of said adhesive top surface of said first kit element and placed on top of said second kit element,
wherein said third kit element is smaller than said first kit element and completely covers said second kit element, and
transversely positioning said third kit element on a user's extremity, wherein said third kit element is positioned between said second kit element and said user's extremity and transversely positioning said second kit element on said third kit element,
adhering a remaining portion of said adhesive top surface of said first kit element to said user's extremity when said device is positioned on said user's extremity and,
optionally assembling a pouch from said first and third kit elements and inserting said second kit element into said pouch, transversely with respect to said first and third kit elements.

2. The method in accordance with claim 1 in which said second semi-rigid material is pre-bent.

3. The three component kit method in accordance with claim 1 in which said second semi-rigid material is bendable.

* * * * *